United States Patent
Mozdzierz et al.

(10) Patent No.: US 9,028,448 B2
(45) Date of Patent: May 12, 2015

(54) ACCESS SEAL WITH INTERSTITIAL CHANNELS

(75) Inventors: Patrick D. Mozdzierz, Rocky Hill, CT (US); Michael Bettuchi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 1060 days.

(21) Appl. No.: 12/434,864

(22) Filed: May 4, 2009

(65) Prior Publication Data
US 2009/0318869 A1 Dec. 24, 2009

Related U.S. Application Data

(66) Substitute for application No. 61/073,804, filed on Jun. 19, 2008.

(51) Int. Cl.
*A61B 17/34* (2006.01)

(52) U.S. Cl.
CPC ......... *A61B 17/3462* (2013.01); *A61B 17/3498* (2013.01); *A61B 17/3423* (2013.01)

(58) Field of Classification Search
USPC ........................................ 604/101.02, 167.03
See application file for complete search history.

(56) References Cited

U.S. PATENT DOCUMENTS

| | | | |
|---|---|---|---|
| 2,319,554 A | 5/1943 | Penn et al. |
| 4,007,909 A | 2/1977 | Buseth et al. |
| 4,126,133 A | 11/1978 | Schwartz |
| 4,177,814 A | 12/1979 | Knepshield et al. |
| 4,473,211 A | 9/1984 | Fremy |
| 4,475,548 A | 10/1984 | Muto |
| 4,586,694 A | 5/1986 | Jones |
| 4,665,752 A | 5/1987 | Huschelrath et al. |
| 4,686,977 A | 8/1987 | Cosma |
| 4,874,378 A | 10/1989 | Hillstead |
| 4,890,612 A | 1/1990 | Kensey |
| 4,917,668 A | 4/1990 | Haindl |
| 4,929,235 A | 5/1990 | Merry et al. |
| 4,960,412 A | 10/1990 | Fink |
| 5,002,557 A | 3/1991 | Hasson |
| 5,123,634 A | 6/1992 | Schwerdt |
| 5,127,626 A | 7/1992 | Hilal et al. |
| 5,197,955 A | 3/1993 | Stephens et al. |
| 5,201,714 A | 4/1993 | Gentelia et al. |
| 5,209,736 A | 5/1993 | Stephens et al. |
| 5,209,737 A | 5/1993 | Ritchart et al. |
| 5,211,633 A | 5/1993 | Stouder, Jr. |
| 5,221,264 A | 6/1993 | Wilk et al. |
| 5,224,930 A | 7/1993 | Spaeth et al. |
| 5,242,412 A | 9/1993 | Blake, III |
| 5,251,873 A | 10/1993 | Atkinson et al. |

(Continued)

FOREIGN PATENT DOCUMENTS

| DE | 20015388 | 3/2001 |
|---|---|---|
| EP | 0567141 | 10/1993 |

(Continued)

*Primary Examiner* — Nicholas Lucchesi
*Assistant Examiner* — Anh Bui (57) ABSTRACT

The present disclosure relates to a valve or seal of the type adapted to allow the introduction of an instrument or object therethrough. In particular, the valve disclosed herein is adapted to maintain a substantially fluid-tight seal with a surgical instrument and is used during a minimally invasive surgical procedure. The valve disclosed herein incorporates one or more bladder members adapted to retain a fluid therein that are associated by one or more interstitial members.

19 Claims, 8 Drawing Sheets

(56) References Cited

U.S. PATENT DOCUMENTS

| | | | |
|---|---|---|---|
| 5,273,545 A | 12/1993 | Hunt et al. | |
| 5,295,657 A | 3/1994 | Atkinson et al. | |
| 5,300,033 A | 4/1994 | Miller | |
| 5,300,035 A | 4/1994 | Clement | |
| 5,300,436 A | 4/1994 | Goldstein et al. | |
| 5,308,336 A | 5/1994 | Hart et al. | |
| 5,338,307 A | 8/1994 | Stephens et al. | |
| 5,342,315 A | 8/1994 | Rowe et al. | |
| 5,350,362 A | 9/1994 | Stouder, Jr. | |
| 5,366,446 A | 11/1994 | Tal et al. | |
| 5,380,288 A | 1/1995 | Hart et al. | |
| 5,385,553 A | 1/1995 | Hart et al. | |
| RE34,866 E | 2/1995 | Kensey et al. | |
| 5,389,080 A | 2/1995 | Yoon | |
| 5,389,081 A | 2/1995 | Castro | |
| 5,391,153 A | 2/1995 | Haber et al. | |
| 5,395,342 A | 3/1995 | Yoon | |
| 5,397,335 A | 3/1995 | Gresl et al. | |
| 5,403,284 A | 4/1995 | Gross | |
| 5,405,330 A | 4/1995 | Zunitch et al. | |
| 5,407,433 A | 4/1995 | Loomas | |
| 5,423,761 A | 6/1995 | Hein et al. | |
| 5,429,609 A | 7/1995 | Yoon | |
| 5,460,616 A | 10/1995 | Weinstein et al. | |
| 5,476,475 A | 12/1995 | Gadberry | |
| 5,492,304 A | 2/1996 | Smith et al. | |
| 5,496,280 A | 3/1996 | Vandenbroek et al. | |
| 5,509,643 A | 4/1996 | Carstens et al. | |
| 5,512,053 A | 4/1996 | Pearson et al. | |
| 5,514,133 A | 5/1996 | Golub et al. | |
| 5,531,758 A | 7/1996 | Uschold et al. | |
| 5,540,661 A | 7/1996 | Tomisaka et al. | |
| 5,545,142 A | 8/1996 | Stephens et al. | |
| 5,554,124 A | 9/1996 | Alvarado | |
| 5,569,205 A | 10/1996 | Hart et al. | |
| 5,569,206 A | 10/1996 | Gorman, Jr. et al. | |
| 5,584,850 A | 12/1996 | Hart et al. | |
| 5,603,702 A | 2/1997 | Smith et al. | |
| 5,607,397 A | 3/1997 | Stephens et al. | |
| 5,613,663 A | 3/1997 | Schmidt et al. | |
| 5,628,732 A | 5/1997 | Antoon, Jr. et al. | |
| 5,634,908 A | 6/1997 | Loomas | |
| 5,653,705 A | 8/1997 | de la Torre et al. | |
| 5,657,963 A | 8/1997 | Hinchliffe et al. | |
| 5,662,615 A | 9/1997 | Blake, III | |
| 5,676,657 A | 10/1997 | Yoon | |
| 5,709,664 A | 1/1998 | Vandenbroek et al. | |
| 5,720,759 A | 2/1998 | Green et al. | |
| 5,752,938 A | 5/1998 | Flatland et al. | |
| 5,755,702 A | 5/1998 | Hillstead et al. | |
| 5,779,697 A | 7/1998 | Glowa et al. | |
| 5,782,817 A | 7/1998 | Franzel et al. | |
| 5,788,676 A * | 8/1998 | Yoon | 604/167.03 |
| 5,792,113 A | 8/1998 | Kramer et al. | |
| 5,797,888 A | 8/1998 | Yoon | |
| 5,814,026 A | 9/1998 | Yoon | |
| 5,820,600 A | 10/1998 | Carlson et al. | |
| 5,820,604 A | 10/1998 | Fox et al. | |
| 5,820,606 A | 10/1998 | Davis et al. | |
| 5,827,228 A | 10/1998 | Rowe | |
| 5,865,817 A | 2/1999 | Moenning et al. | |
| 5,868,714 A | 2/1999 | Danks | |
| 5,871,471 A | 2/1999 | Ryan et al. | |
| 5,879,368 A | 3/1999 | Hoskin et al. | |
| 5,895,377 A | 4/1999 | Smith et al. | |
| 5,906,595 A | 5/1999 | Powell et al. | |
| 5,913,847 A | 6/1999 | Yoon | |
| 5,941,815 A | 8/1999 | Chang | |
| 5,989,224 A | 11/1999 | Exline et al. | |
| 5,989,232 A | 11/1999 | Yoon | |
| 5,989,233 A * | 11/1999 | Yoon | 604/523 |
| 5,993,471 A | 11/1999 | Riza et al. | |
| 5,997,515 A | 12/1999 | De La Torre et al. | |
| 6,000,670 A | 12/1999 | Okamoto | |
| 6,030,403 A | 2/2000 | Long et al. | |
| RE36,702 E | 5/2000 | Green et al. | |
| 6,066,177 A | 5/2000 | Hatsuda | |
| 6,068,011 A | 5/2000 | Paradis | |
| 6,077,249 A | 6/2000 | Dittrich et al. | |
| 6,077,288 A | 6/2000 | Shimomura et al. | |
| 6,083,203 A | 7/2000 | Yoon | |
| 6,093,176 A | 7/2000 | Dennis | |
| 6,110,154 A | 8/2000 | Shimomura et al. | |
| 6,123,689 A | 9/2000 | To et al. | |
| 6,159,182 A | 12/2000 | Davis et al. | |
| 6,176,843 B1 | 1/2001 | DiCaprio et al. | |
| 6,197,002 B1 | 3/2001 | Peterson | |
| 6,217,555 B1 | 4/2001 | Hart et al. | |
| 6,238,373 B1 * | 5/2001 | de la Torre et al. | 604/256 |
| 6,254,570 B1 * | 7/2001 | Rutner et al. | 604/101.02 |
| D449,887 S | 10/2001 | Haberland et al. | |
| 6,468,292 B1 | 10/2002 | Mollenauer et al. | |
| 6,482,181 B1 | 11/2002 | Racenet et al. | |
| 6,551,282 B1 | 4/2003 | Exline et al. | |
| 6,595,946 B1 | 7/2003 | Pasqualucci | |
| 6,702,787 B2 | 3/2004 | Racenet et al. | |
| 6,942,671 B1 | 9/2005 | Smith | |
| 6,958,069 B2 | 10/2005 | Shipp et al. | |
| 7,011,314 B2 | 3/2006 | McFarlane | |
| 7,163,510 B2 | 1/2007 | Kahle et al. | |
| 7,169,130 B2 | 1/2007 | Exline et al. | |
| 7,214,185 B1 | 5/2007 | Rosney et al. | |
| 7,235,062 B2 | 6/2007 | Brustad | |
| 7,481,765 B2 | 1/2009 | Ewers et al. | |
| 7,582,071 B2 | 9/2009 | Wenchell | |
| 7,608,082 B2 | 10/2009 | Cuevas et al. | |
| 2002/0137988 A1 | 9/2002 | Shipp et al. | |
| 2002/0156432 A1 | 10/2002 | Racenet et al. | |
| 2002/0183594 A1 | 12/2002 | Beane et al. | |
| 2002/0188319 A1 | 12/2002 | Morris et al. | |
| 2003/0019554 A1 | 1/2003 | Agostini et al. | |
| 2003/0139756 A1 | 7/2003 | Brustad | |
| 2003/0172941 A1 | 9/2003 | Streifinger et al. | |
| 2004/0106942 A1 | 6/2004 | Taylor et al. | |
| 2007/0085232 A1 | 4/2007 | Brustad et al. | |
| 2008/0269696 A1 | 10/2008 | Exline et al. | |
| 2009/0049617 A1 * | 2/2009 | Chaffee | 5/706 |
| 2009/0234293 A1 * | 9/2009 | Albrecht et al. | 604/167.02 |

FOREIGN PATENT DOCUMENTS

| | | |
|---|---|---|
| EP | 0674879 | 4/1995 |
| EP | 1679043 | 7/2006 |
| EP | 1681030 | 7/2006 |
| EP | 2050403 | 4/2009 |
| WO | WO 94/22357 | 10/1994 |
| WO | WO 94/26349 | 11/1994 |
| WO | WO 98/44983 | 10/1998 |
| WO | 9848724 | 11/1998 |
| WO | WO 99/29250 | 6/1999 |
| WO | 9942152 | 8/1999 |
| WO | 03015848 | 2/2003 |
| WO | WO 03/034908 A2 | 5/2003 |

* cited by examiner

ACCESS SEAL WITH INTERSTITIAL CHANNELS

CROSS REFERENCE TO RELATED APPLICATION

The present application claims the benefit of and priority to U.S. Provisional Application Ser. No. 61/073,804 filed on Jun. 19, 2008, the entire contents of which are incorporated herein by reference.

BACKGROUND

1. Technical Field

The present disclosure relates to a valve or seal of the type adapted for the sealed reception of an object. In particular, this disclosure relates to a valve or seal for use with a surgical portal system such as a cannula or trocar assembly.

2. Background of the Related Art

Today, many surgical procedures are performed through portal or access devices such as trocar and cannula assemblies. These devices incorporate narrow tubes or cannulas percutaneously inserted into a patient's body, through which surgical instruments are introduced and manipulated during the course of the procedure. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

Generally, during minimally invasive procedures, prior to the introduction of a surgical instrument into the patient's body, insufflation gasses are used to enlarge the area surrounding the target surgical site to create a larger, more accessible work area. Accordingly, the maintenance of a substantially fluid-tight seal along the central opening of the access device, in both the presence and absence of a surgical instrument, is crucial so as to prevent the escape of the insufflation gases and the deflation or collapse of the enlarged surgical work area. To this end, access devices generally incorporate a valve or seal member. Various types of valves and seals are known in the art, examples of which may be seen in commonly owned U.S. Pat. No. 5,512,053 to Pearson, the entire contents of which are hereby incorporated by reference.

During the course of a minimally invasive procedure, a clinician will frequently move surgical instruments laterally within the access device, and the valve, to access different regions of the surgical site. This lateral movement may cause the valve to stretch and deform, thereby causing the leakage of insufflation gas around the instrument. In addition, a clinical will often employ instrumentation of various sizes and diameters during the course of a procedure.

While many varieties of valve are known in the art, a continuing need exists for a valve that can accommodate both the lateral movement of an instrument inserted therethrough, as well as instruments of various sizes, while maintaining the integrity of an insufflated workspace.

SUMMARY

The present disclosure is directed to a valve that defines includes a passage configured and dimensioned for the sealed reception of an elongated object. In one embodiment, a surgical valve is disclosed for use with a surgical portal apparatus. The surgical valve defines a passage therethrough and includes at least one membrane and at least two bladder members disposed therein. In one embodiment, the at least two bladder members are connected to the at least one membrane. The at least two bladder members are each configured to retain a fluid therein and are in fluid communication with one another. The at least one membrane may be formed of an at least semi-resilient material and may include inner and outer membranes that define a first cavity therebetween. In one embodiment, the at least two bladder members are disposed within the first cavity.

The surgical valve may further include a first fluid disposed within each of the at least two bladder members, a second fluid disposed within the cavity and surrounding the at least two bladder members, and at least one interstitial member. The at least one interstitial member is disposed between the at least two bladder members. The at least one interstitial member may define a lumen therethrough that is configured to facilitate the communication of fluid between the at least two bladder members.

In an alternate embodiment, the at least two bladder members are arranged in a substantially annular configuration within the cavity. The present disclosure further contemplates that the at least two bladder members may be arranged in two or more concentric rings which may include an inner ring and an outer ring.

In another aspect of the present disclosure, a valve is disclosed that defines an opening therethrough that is adapted for the sealed reception of an object. The valve includes at least one membrane and a plurality of bladder members disposed within the at least one membrane. The plurality of bladder members are each configured to retain a fluid therein and are in fluid communication such that the valve may transition from a first condition to a second condition.

In one embodiment, the valve further includes at least one interstitial member or channel that is disposed between adjacent bladder members. The at least one interstitial member defines a lumen therethrough that is in substantial alignment with at least one aperture formed in each of the plurality of bladder members such that the lumen of the interstitial member and the aperture are in fluid communication.

These and other features of the valve disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein.

DETAILED DESCRIPTION OF THE EMBODIMENTS

In the drawings and in the description which follows, in which like references numerals identify similar or identical elements, the term "proximal" will refer to the end of the apparatus which is closest to the clinician, while the term "distal" will refer to the end which is furthest from the clinician, as is traditional and known in the art.

Figure 1:
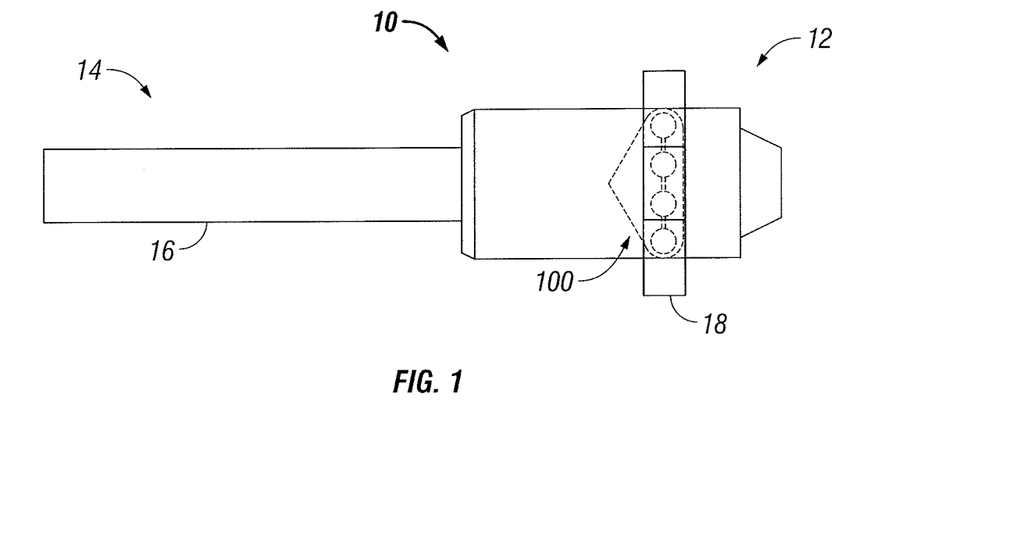
FIG. 1 is a side schematic view of a valve in accordance with the principles of the present disclosure disposed within a cannula assembly.

With reference to FIG. 1, a reusable cannula assembly 10 is illustrated. Cannula assembly 10 has proximal and distal ends 12, 14, a shaft or elongate member 16 disposed therebetween, and a valve or seal housing 18. Disposed within valve housing 18 is a valve 100 that is the subject of the present disclosure.

Valve housing 18 may be any structure suitable for the intended purpose of accommodating valve 100. Further information regarding valve housing 18 may be obtained through reference to commonly owned U.S. Pat. No. 7,169,130 to Exline et al., the entire contents of which are hereby incorporated by reference.

Extending distally from valve housing 18 is a shaft or elongate member 16 that is configured for the internal receipt of an obturator or similar surgical instrument (not shown). At its distal end 14, cannula assembly 10 is open and configured to allow the obturator (not shown) to pass therethrough such that percutaneous access to a patient's internal cavities may be achieved.

Figure 2:
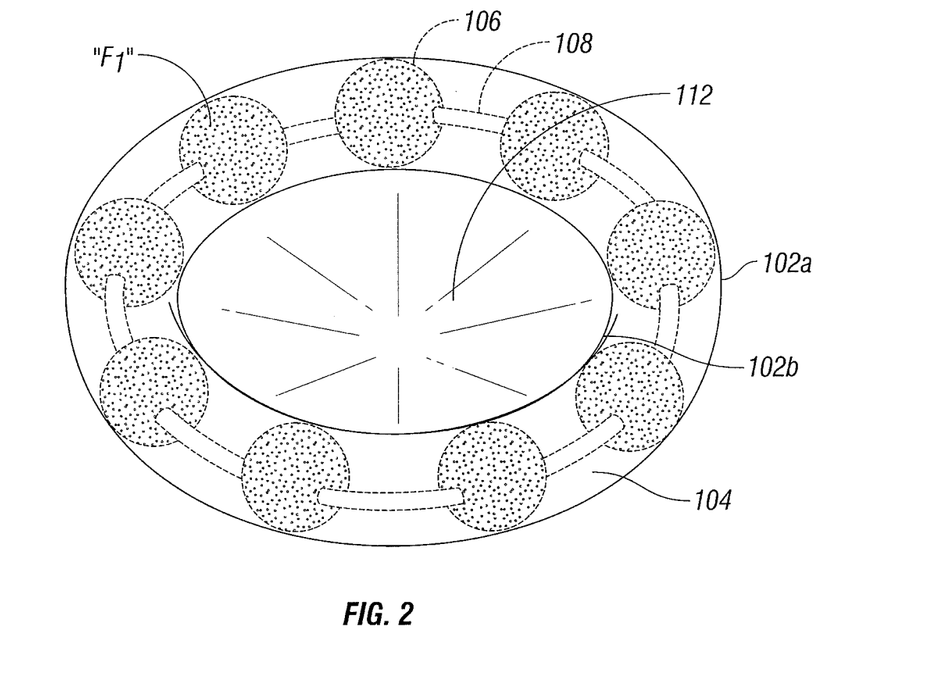
FIG. 2 is a side perspective and schematic view of the valve of FIG. 1 shown in a second position.
Figure 3:
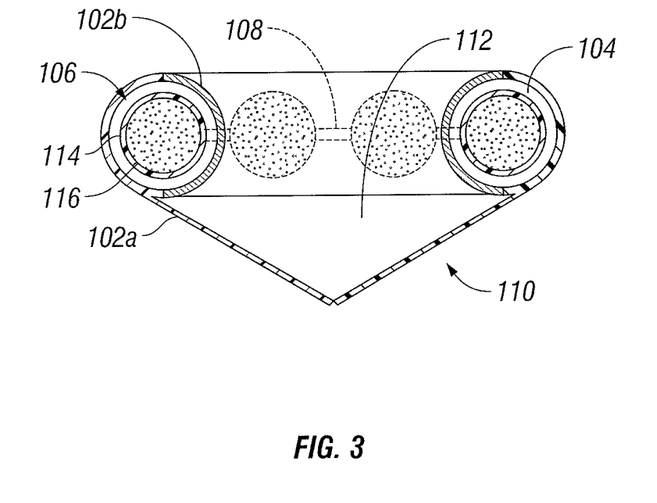
FIG. 3 is a side cross-sectional view of the valve of FIGS. 1-2 shown in a first position.
Figure 4:
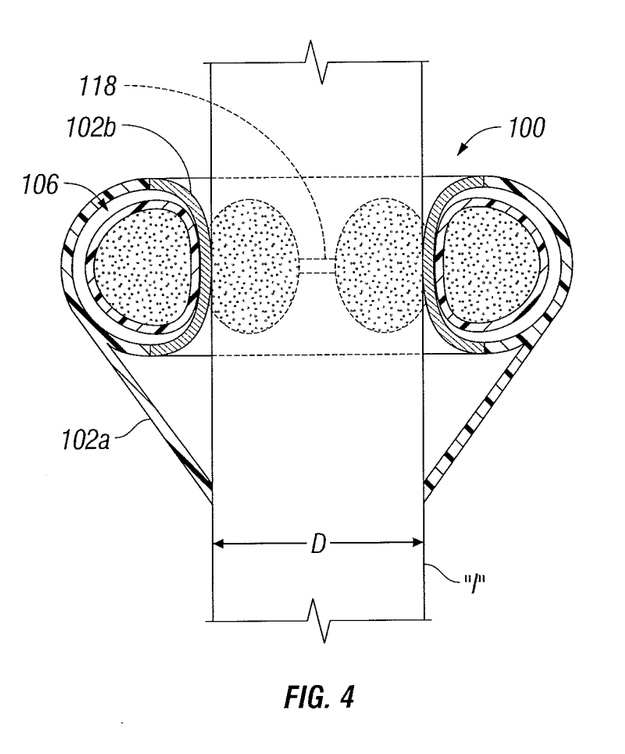
FIG. 4 is a side cross-sectional view of the valve of FIGS. 1-3 shown in the second condition with a surgical instrument inserted therethrough.

Referring now to FIGS. 2-4, valve 100 will be discussed. Valve 100 includes outer and inner membranes 102a, 102b, respectively, and two or more bladder members 106 associated with one another by at least one interstitial member or channel 108. As seen in FIGS. 3-4, valve 100 has a generally downward conical shape 110 that facilitates the insertion of an object, e.g. a medical instrument "I", without substantially tearing or damaging the valve 100.

Outer and inner membranes 102a, 102b of valve 100 define a first cavity 104 therebetween and are each formed from any suitable biocompatible material that is at least semi-resilient in nature. The at least semi-resilient material permits the respective outer and inner membranes 102a, 102b to resiliently deform or stretch upon the insertion of a surgical instrument, as discussed in further detail below.

Outer membrane 102a and inner membrane 102b define an opening or passage 112 through valve 100 that is dimensioned to sealingly receive an instrument or object "I", e.g. a surgical instrument. Valve 100 is adapted to transition from a first condition to a second condition upon the insertion of instrument "I", as described in further detail below.

In the first position, seen in FIG. 3, valve 100 is at rest and passage 112 is substantially closed, thereby preventing the escape of any insufflation gases through either valve 100 or the proximal end of cannula assembly 10 in the absence of a surgical instrument. As seen in FIG. 4, upon the insertion of instrument "I" into valve 100, valve 100 transitions into the second condition in which the dimensions of passage 112 closely approximate those of the instrument "I" inserted therethrough, e.g. diameter "D" of instrument "I", such that valve 100 forms a substantially fluid-tight seal therewith, thereby substantially preventing the escape of any insufflation gases. The diameter "D" of the instrument "I", and thus the dimensions of passage 112 in the second condition, will generally lie within the range of approximately 5 mm to approximately 15 mm, as is conventional to the art.

Disposed within first cavity 104 defined by outer and inner membranes 102a, 102b are at least two bladder members 106, each of which are substantially identical. Bladder members 106 are defined by an outer wall 114 that defines a second cavity 116. The present disclosure contemplates that outer wall 114 may be formed of any suitable biocompatible material that is at least semi-resilient in nature and capable of retaining a fluid therein. As discussed above with respect to the outer and inner membranes 102a, 102b, respectively, the at least semi-resilient material permits the bladder member 106 to resiliently deform or stretch upon the insertion of a surgical instrument, as discussed in further detail below.

Figure 5:
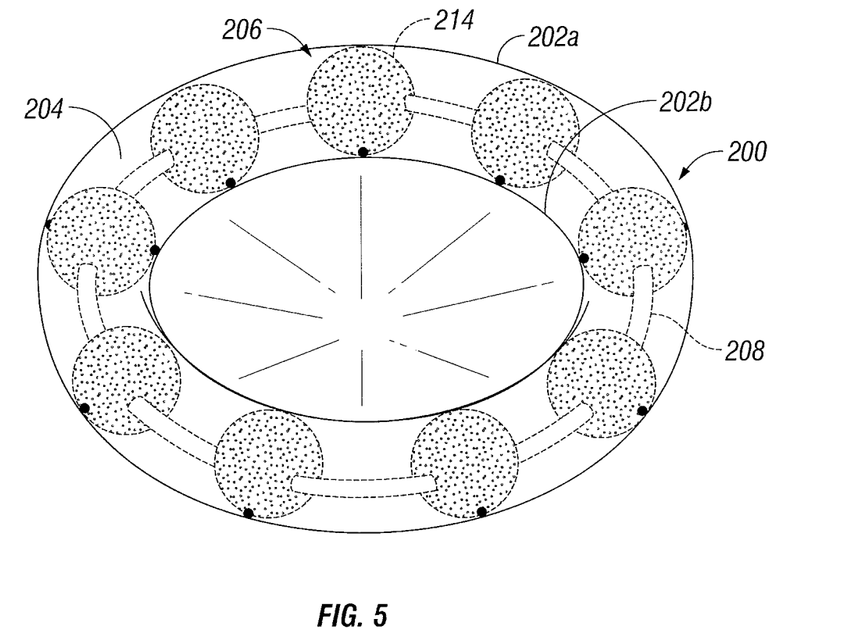
FIG. 5 is a side perspective and schematic view of another embodiment of the valve.

As seen in the embodiment of FIGS. 1-4, outer walls 114 of bladder members 106 of valve 100 are defined by outer walls 114 that are free from connection with either outer membrane 102a or inner membrane 102b such that bladder members 106 may traverse first cavity 104. As seen in FIG. 5, in an alternate embodiment, outer walls 214 of bladder members 206 are fixedly connected to either or both of outer and inner membranes 202a, 202b, respectively, such that bladder members 206 maintains a substantially constant position within first cavity 204 of valve 200 during use.

Referring again to FIGS. 1-4, outer wall 114 of bladder member 106 retains a pre-determined volume of a first fluid "$F_1$" therein. First fluid "$F_1$" may be any suitable biocompatible fluid including, but not limited to water, saline, or air. As would be appreciated by one of ordinary skill in the art, first fluid "$F_1$" provides a measure of structure and rigidity to bladder member 106, while allowing bladder member 106 to resiliently deform under the influence of an external force, as described in further detail below. As would be appreciated by one of ordinary skill, the resiliency of bladder member 106 may be regulated or controlled in various embodiments of valve 100 by varying either or both of the volume or composition of fluid "$F_1$".

The resilient nature of valve 100, achieved through the incorporation of at least semi-resilient materials and the inclusion of at least one internal fluid, e.g. fluid "$F_1$", allows valve 100 to exhibit various degrees of deformation during use. This facilitates the accommodation of instruments of various sizes as well as the maintenance of a substantially fluid-tight seal therewith during axial or lateral movement of an instrument within valve 100, as described in further detail below.

It is contemplated herein that the dimensions of bladder members 106 may vary within the strictures of valve 100. The present disclosure further contemplates the incorporation of any suitable number of bladder members 106 within valve 100. In addition, bladder members 106 having various geometrical configurations, including but not limited to spherical, torroidal, or elliptical are also within the scope of the present disclosure.

As indicated above, bladder members 106 are associated with one another by at least one interstitial member 108. Interstitial member, or members, 108 are formed of any at least semi-resilient biocompatible material. This at least semi-resilient material permits the interstitial members 108 resiliently deform or stretch upon the insertion of a surgical instrument, as discussed in further detail below.

Interstitial members 108 assist in maintaining the respective orientation of adjacent bladder members 106 within the first cavity 104 defined by outer and inner membranes 102a, 102b of valve 100.

In the embodiment of FIGS. 1-4, valve 100 includes bladder members 106 and interstitial members 108 that are arranged in a substantially annular configuration. The present disclosure also contemplates that the bladder members and interstitial members may be arranged in any other suitable configuration, e.g. a lattice or matrix.

Figure 6:
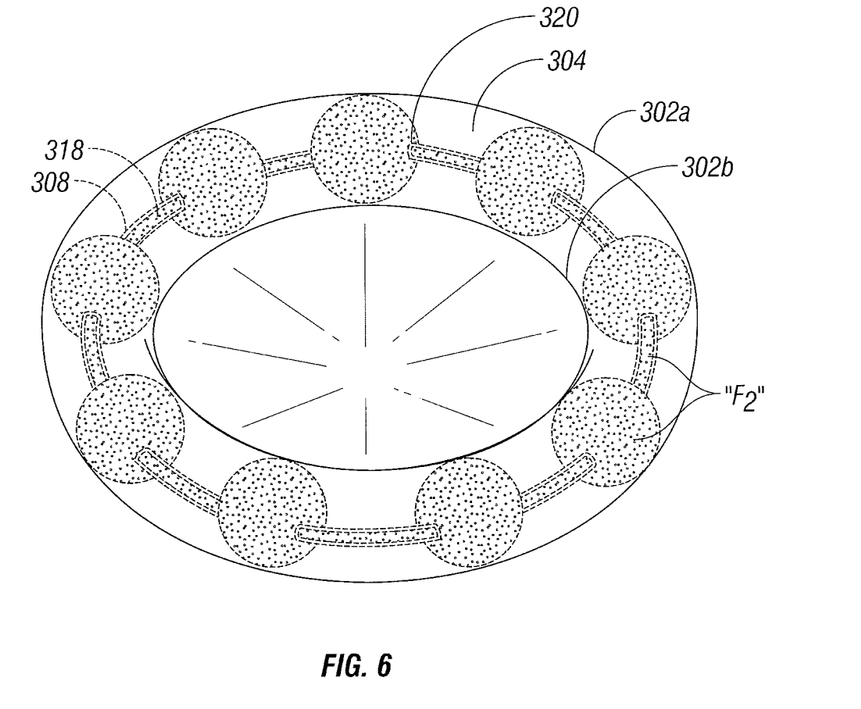
FIG. 6 is a side perspective and schematic view of another embodiment of the valve including a plurality of interstitial members, each with a lumen defined therethrough.

In the embodiments of FIGS. 1-4 and FIG. 5, interstitial members 108 and 208, respectively, are solid, connective members. In an alternate embodiment, seen in FIG. 6, interstitial members 308 each define a lumen 318 therethrough. As with the previous embodiments, interstitial members 308 are disposed between adjacent bladder members 306 within a first cavity 304 defined by outer and inner membranes 302a, 302b. In this embodiment, bladder members 306 each have an outer wall 314 that retains a fluid "$F_2$" therein and includes at least one aperture 320. Lumen 318 of interstitial member 308 and aperture 320 are substantially aligned such that the fluid "$F_2$" disposed within each bladder member 306 may be communicated therebetween through lumen 318. The dimensions of aperture 320 and lumen 318 of the interstitial member 308 may be varied in any matter suitable for the intended purpose of establishing fluid communication between adjacent bladder members 306.

Figure 7:
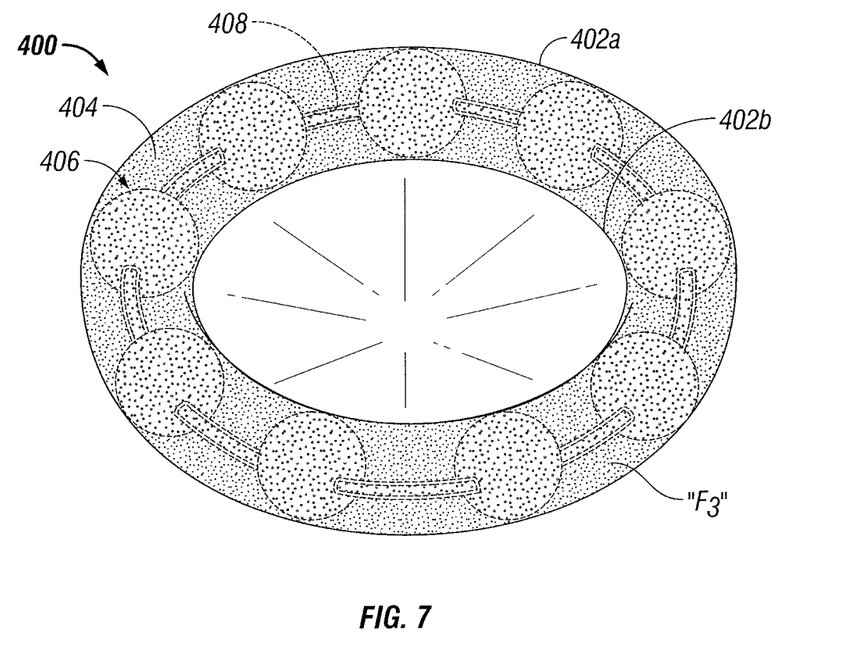
FIG. 7 is a side perspective and schematic view of another embodiment of the valve.

Referring now to FIG. 7, in another aspect of the present disclosure, a second fluid "$F_3$" is disposed about bladder members 406 and interstitial members 408 within first cavity 404 defined by outer and inner membranes 402a, 402b, respectively. Fluid "$F_3$" may be any suitable biocompatible fluid including, but not limited to water, saline, or air. As discussed above with respect to the embodiment of FIGS. 1-4, fluid "$F_3$" provides a measure of structure and rigidity to valve 400 as well as resiliency by allowing the inner membrane 402b to deform under the influence of an external force, as described in further detail below.

Figure 8:
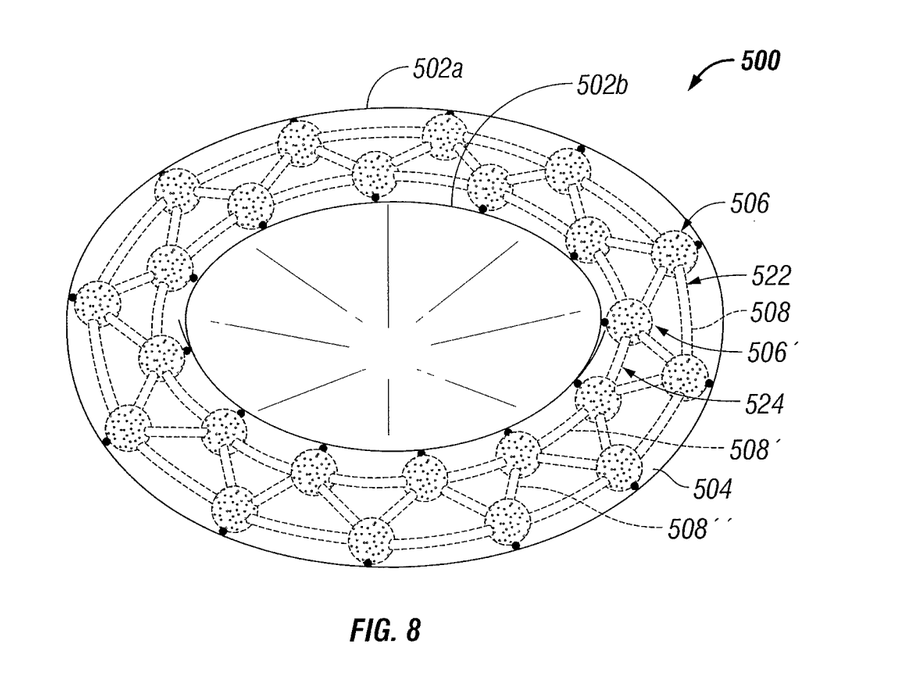
FIG. 8 is a side perspective and schematic view of another embodiment of the valve that includes at least one concentric ring of bladders.

As seen in FIG. 8, in another embodiment, valve 500 may include a plurality of bladder members 506, 506' arranged in at least one concentric ring 522, 524 within cavity 504 defined by respective outer and inner membranes 502a, 502b. In particular, bladder members 506 are arranged in a first or outer ring 522 and bladder members 506' are arranged in a second or inner ring 524. While FIG. 8 depicts two concentrically arranged rings of bladder members disposed in horizontal relation, additional rings and bladder members, and additional configurations therefore, e.g. rings disposed in vertical relation to one another, are also within the scope of the present disclosure. As with the embodiments discussed above in FIGS. 1-7, adjacent bladder members 506 of the outer ring 522 and adjacent bladder members 506' of the inner ring 524 are associated by a plurality of interstitial members 508, 508', respectively. The interstitial members may be solid, connective members, or may define a lumen therethrough, such that fluid may be communicated between adjacent bladder members, as discussed above with respect to the embodiment of FIG. 6. Outer and inner rings 522, 524, respectively, may be associated by interstitial members 508" such that relative movement of the inner and outer rings 522, 524 is substantially inhibited. The present disclosure also contemplates that the respective outer and inner rings 522, 524 may be free from connection with one another such that relative movement may occur. Interstitial members 508" may also define a lumen therethrough such that fluid may also be communicated between the bladder members 506 of the outer ring 522 and the bladder members 506' of the inner ring 524.

Bladder members 506 of outer ring 522 and bladder members 506' of inner ring 524 are connected to outer and inner membranes 502a and 502b, respectively, such that outer ring 522 and inner ring 524 maintain a substantially constant position within first cavity 504 when valve 500 is in use, as discussed above with respect to the embodiments of FIG. 5. In an alternate embodiment, bladder members 506 and 506' of outer and inner rings 522, 524, respectively, are free from connection with either of outer membranes 502a or inner membrane 502b such that outer ring 522 and inner ring 524 may move within first cavity 504 during the use of valve 500, as discussed above with respect to the embodiment of FIGS. 1-4.

Figure 9:
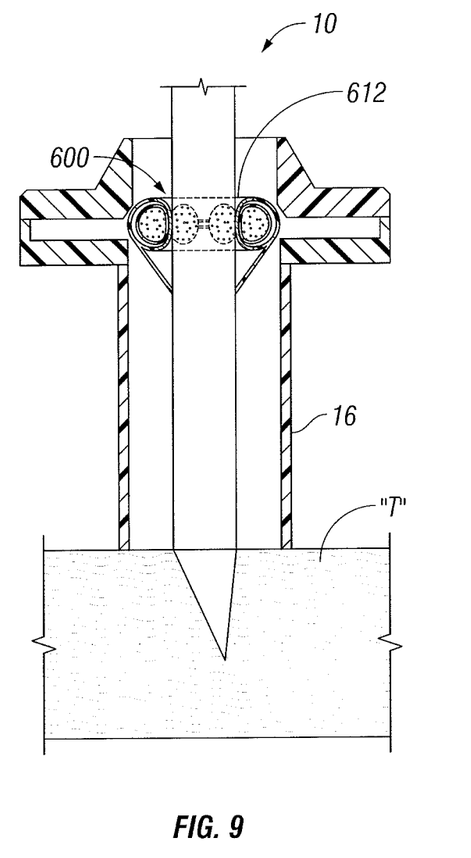
FIG. 9 is a side cross-sectional view of the valve disposed in a cannula assembly with a surgical instrument inserted therethrough.
Figure 10:
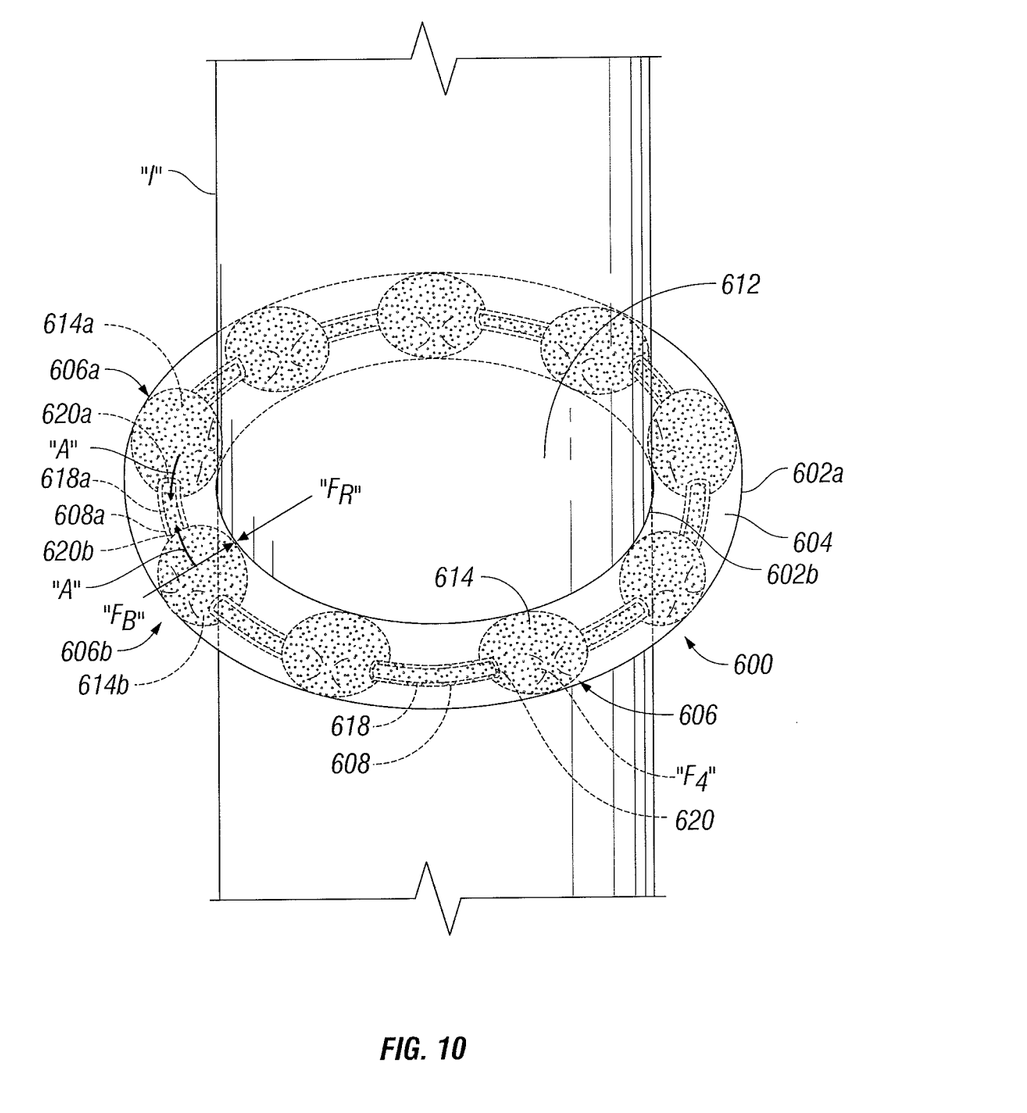
FIG. 10 is a side perspective and schematic view of the valve of FIG. 9 with the instrument inserted therethrough.

Referring now to FIGS. 9-10, the use and function of a valve 600 will be described in conjunction with a surgical portal apparatus, e.g., cannula assembly 10. Consistent with the embodiment of FIG. 6, valve 600 has outer and inner membranes 602a, 602b, respectively, that define a first cavity 604. Disposed within first cavity 604 are bladder members 606. Bladder members 606 have outer walls 614 that retain a fluid "$F_4$" therein and include at least one aperture 620. Adjacent bladder members 606 are associated by a plurality of interstitial members 608 that each define a lumen 618 therethrough.

Initially, the target site is insufflated with a suitable biocompatible gas, e.g., $CO_2$ gas, such that a larger internal workspace may be created within a patient, thereby providing greater access to the patient's internal organs. The insufflation may be performed with an insufflation needle or similar device, as is conventional in the art. Following insufflation, an obturator (not shown), or the like, is advanced distally through elongate member 16 of cannula assembly 10 and a valve 100 disposed therein until a percutaneous access point is created in the patient's tissue "T", as is also commonly known in the art. Thereafter, cannula assembly 10 is positioned within the access point and the obturator (not shown) is withdrawn. Subsequently, a surgical instrument "I" is inserted into cannula assembly 10 through a passage or opening 612 formed in valve 600. Upon the insertion of instrument "I", and during the distal advancement thereof, valve 600 transitions from the first condition to the second condition, as discussed above with respect to the embodiment of FIGS. 1-4, under the influence of an external force "$F_R$" directed radially outward that is exerted upon inner membrane 602b by instrument "I". Radial force "$F_R$" causes inner membrane 602b to outwardly deform or stretch and is transmitted from inner membrane 602b to bladder members 606 and to the fluid "$F_4$" retained therein. The influence of force "$F_R$" upon bladder members 606 and interstitial members 608 will be discussed with respect to a pair of exemplary bladder member 606a and 606b and an exemplary interstitial member 608a only. It should be understood, however, that the following discussion is descriptive of that which occurs within each bladder member 606 and each interstitial member 608.

Under the influence of force "$F_R$", outer walls 614a, 614b of bladder members 606a and 606b, respectively, deform inwardly as well. This deformation decreases the overall volume of bladder members 606a and 606b, thereby displacing fluid "$F_4$" both radially within each bladder member 606a and 606b and circumferentially through apertures 620a in the direction of arrows "A". The radial displacement of fluid "$F_4$" forces outer walls 614a against outer membrane 602a, causing outer membrane 602a to outwardly deform as well and increasing the overall radius of valve 600. The fluid "$F_4$" that is displaced circumferentially through apertures 620a enters interstitial member 608a and may be communicated therethrough and into an adjacent bladder member through the lumen 618a of interstitial member 608a. The displaced fluid causes either or both of bladder members 606a and 606b, as well as interstitial member 608a, to stretch or deform. As discussed above, inner membrane 602b, outer membrane 602a, bladder members 606a and 606b, and interstitial member 608a are each formed of an at least semi-resilient material. The natural tendency of this material, as well as that of displaced fluid "$F_4$", to return to an initial or undeformed position creates a biasing force "$F_B$" that is directly related in magnitude to that of radial force "$F_R$". Biasing force "$F_B$" is directed radially inward and acts upon each of bladder members 606a and 606b, interstitial member 608a, and inner membrane 602b, which transmits the force to instrument "I". Accordingly, biasing force "$F_B$" urges valve 600 back into the first condition, while maintaining the position of instrument "I" and creating a substantially fluid-tight seal therewith.

Figure 11:
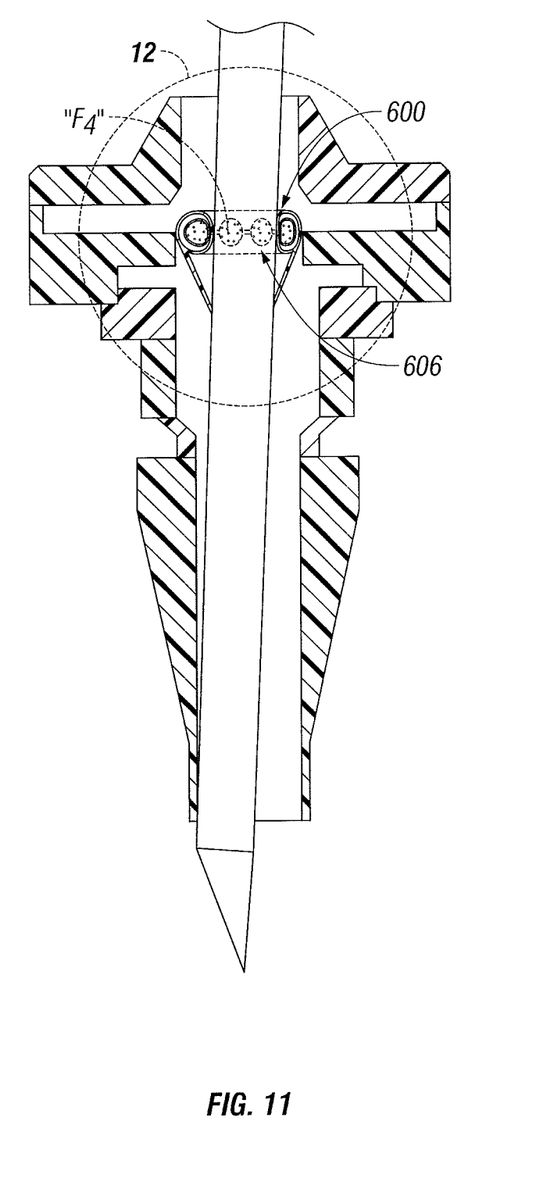
FIG. 11 is a side cross-sectional view of the valve of FIG. 9 with the instrument biased to the right.
Figure 12:
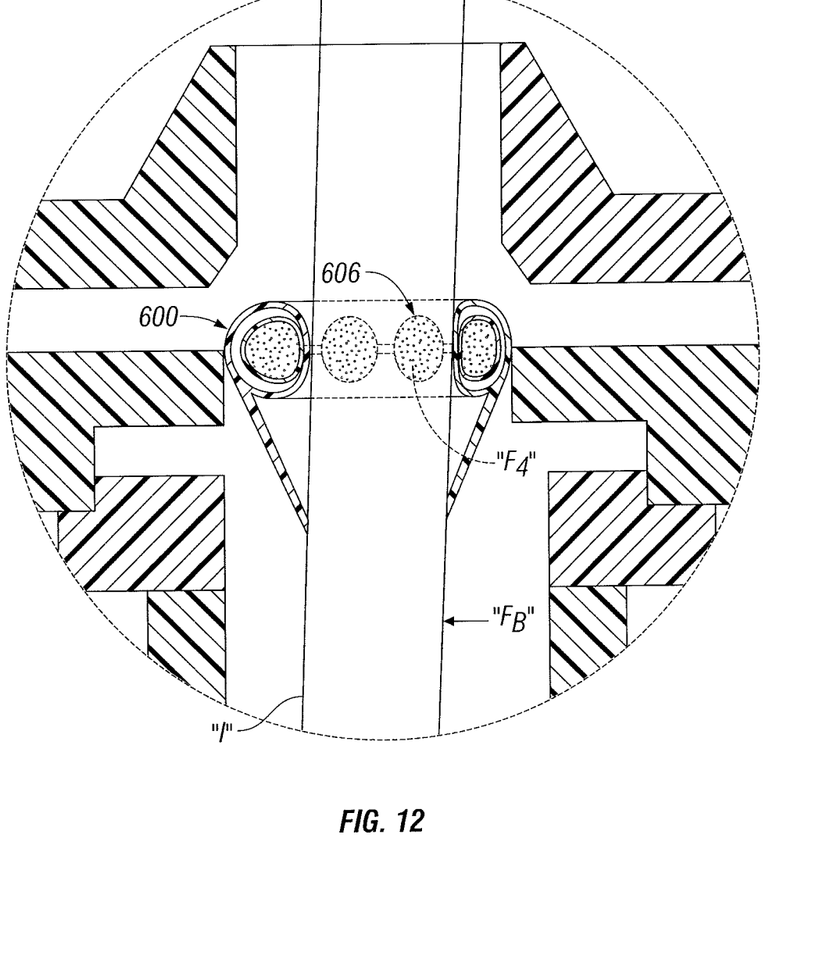
FIG. 12 is a side cross-sectional view of the valve of FIG. 11.

As discussed above, during the course of a minimally invasive procedure, it is often necessary to axially or laterally manipulate a surgical instrument in an effort to access different areas of the surgical site. FIG. 11 describes the impact of such lateral movement upon valve 600. As would be appreciated by one of ordinary skill, axially moving instrument "I" to the right attempts to stretch or deform valve 600 in that direction and causes additional fluid "$F_4$" to be displaced from those bladder members 606 on the right side of the valve 600, resulting in an increased measure of deformation thereof. The additional displacement of fluid "$F_4$" from the bladder members 606 on the right side of the valve 600 increases the magnitude of biasing force "$F_B$" discussed above. Therefore, as instrument "I" is moved laterally, e.g. to the right, biasing force "$F_B$" acts in the opposite direction to create a substantially fluid tight seal with instrument "I" and to urge instrument "I" back into the vertical position.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical portal apparatus, which comprises:
    a portal member defining a longitudinal axis and having a longitudinal opening for passage of a surgical object, the portal member dimensioned for insertion through body tissue to provide access to an underlying surgical site; and
    a valve mounted to the portal member and defining a valve axis extending therethrough, the valve dimensioned and adapted for reception of the surgical object in substantial sealed relation therewith, the valve including:
        at least one membrane defining a passage for introduction of the surgical object and having an internal cavity; and
        at least two bladder members disposed within the internal cavity of the at least one membrane, the at least two bladder members each having a fluid therein and being arranged in spaced relation with respect to the valve axis to at least partially surround the passage of the at least one membrane, the at least two bladder members cooperating with the at least one membrane to establish the substantial sealed relation with the surgical object.

2. The surgical portal apparatus of claim 1, wherein the at least one membrane includes an inner membrane segment and an outer membrane segment.

3. The surgical portal apparatus of claim 1, wherein the at least one membrane is formed of an at least semi-resilient material.

4. The surgical portal apparatus of claim 1, wherein the at least two bladder members are connected to the at least one membrane.

5. The surgical portal apparatus of claim 2, wherein the inner and outer membrane segments define the internal cavity therebetween.

6. The surgical portal apparatus of claim 5, further including a first fluid disposed within each of the at least two bladder members.

7. The surgical portal apparatus of claim 6, further including a second fluid disposed within the internal cavity of the at least one membrane and surrounding the at least two bladder members.

8. The surgical portal apparatus of claim 6, further including at least one interstitial member disposed between the at least two bladder members, the at least one interstitial member is configured to facilitate communication of fluid between the at least two bladder members.

9. The surgical portal apparatus of claim 8, wherein the at least one interstitial member defines a lumen therethrough.

10. The surgical portal apparatus of claim 8 wherein the at least two bladder members are arranged in a substantially annular configuration within the cavity.

11. The surgical portal apparatus of claim 10, wherein the at least two bladder members are arranged in at least two concentric rings within the cavity.

12. The surgical portal apparatus of claim 11, wherein the at least two concentric rings include an inner ring and an outer ring.

13. A surgical portal apparatus, which comprises:
    a portal member defining a longitudinal axis and having a longitudinal opening for passage of a surgical object, the portal member dimensioned for insertion through body tissue to provide access to an underlying surgical site; and
    a valve mounted to the portal member and defining a valve axis extending therethrough, the valve dimensioned and adapted for reception of the surgical object in substantial sealed relation therewith, the valve including:
        a valve membrane; and
        a plurality of bladder members disposed within the valve membrane, the bladder members being in fluid communication and having a fluid dimensioned to communicate between the bladder members to accommodate manipulation of the surgical object.

14. The surgical portal apparatus of claim 13, wherein each of the plurality of bladder members defines at least one aperture that is in fluid communication with at least one interstitial member, the at least one interstitial member being disposed between adjacent bladder members.

15. The surgical portal apparatus of claim 14, wherein the at least one interstitial member defines a lumen therethrough that is substantially aligned with the at least one aperture.

16. The surgical portal apparatus of claim 7 wherein the first fluid is different from the second fluid.

17. The surgical portal apparatus of claim 16 wherein one of the first and second fluids includes air.

18. The surgical portal apparatus of claim 17 wherein the first and second fluids are liquids.

19. The surgical portal apparatus of claim 7 wherein one of the first and second fluids includes air.

\* \* \* \* \*